United States Patent [19]

Voerman

[11] Patent Number: 5,316,760
[45] Date of Patent: May 31, 1994

[54] MOUTH-CARE PRODUCTS

[75] Inventor: Gerard Voerman, Ridderkerk, Netherlands

[73] Assignee: Rodriso Holding B.V., Ridderkerk, Netherlands

[21] Appl. No.: 2,542

[22] Filed: Jan. 11, 1993

Related U.S. Application Data

[63] Continuation of Ser. No. 613,655, Jan. 2, 1991, abandoned.

[30] Foreign Application Priority Data

May 9, 1988 [NL] Netherlands .......................... 8801214

[51] Int. Cl.$^5$ ................................................ A61K 7/26
[52] U.S. Cl. .................................... 424/58; 424/195.1
[58] Field of Search .............................. 424/58, 195.1

[56] References Cited

FOREIGN PATENT DOCUMENTS 54-27514  8/1980  Japan .
55-120509 9/1980  Japan .
558675    5/1977  U.S.S.R. .
615932    7/1978  U.S.S.R. .
712087    1/1980  U.S.S.R. .

OTHER PUBLICATIONS

Ca 8107(24): 223327r, Ariton, et al, Tablet for the Treatment of buccopharyngeal diseases, 1986.
Ca 78(10): 62202m, Kostantinov, et al, Toothpaste, 1972.

Primary Examiner—Marianne M. Cintins
Assistant Examiner—Rebecca Cook
Attorney, Agent, or Firm—Cooper & Dunham

[57] ABSTRACT

The invention relates to mouthcare-products, such as toothpastes, mouthrinses etc. which contain a combination of an *Urtica dioica* extract and a *Juniperus communis* extract. Such a combination leads to a synergistic reduction of both dental plaque and bleeding or inflammation of the gingiva. A further improvement may be obtained by adding an *Achillaea millefolium* extract.

4 Claims, No Drawings

MOUTH-CARE PRODUCTS

This is a continuation of application Ser. No. 07/613,655, filed Jan. 2, 1991 now abandoned.

This invention relates to mouthcare-products such as toothpastes, mouth rinsing liquids and medicinal mouthcare-compositions.

Well known toothpastes (as a paste, liquid form or as a powder form), mouth rinsing liquids (mouthwashes) and medicinal mouthcare preparations (e.g. preparations for treatment of the soft tissues, more particularly of the gingiva, which preparations are most often applied by a treating doctor, dentist or medicinal specialist) usually contain compounds which are known for the required action. Those compounds can largely be divided into ingredients counteracting tooth-decay (caries), like many fluoride-containing substances, and ingredients inhibiting gingival inflammation. Besides those, one or more carriers or diluents, and all other sorts of additions like flavouring-, smell- and colouring-agents, conservation-agents, and, in the case of toothpastes scouring and polishing agents and surfactants are added.

It is well known to add to toothpastes and mouthrinses an extract of *Chamomille folia* in a dosage of 0.1-2.0% by weight (Kitagaki et al.: Antib. Antifung. Agents 11 (8), 1983, pp. 451-461). This extract is antibacterial on microbiota of the mouth and can therefore be used against certain inflammations in the mouth. At higher dosage however, there is a danger of soft tissue irritations, while at lower dosages, it is not effective. The "minimum inhibiting concentration" of this extract differs for various kinds of micro-organisms. For strict anaerobes, the "m.i.c." is 0.15% by weight, for facultative anaerobes, the "m.i.c." is 0.25% by weight. For safety reasons an optimal dosage can be obtained between 0.3 and 1.5% by weight.

Other well known additions in toothpastes and mouthrinses against gingival problems are a.o.: Sodium-acetarsol, sodium-ricinolaat, azulene, alpha-bisabolol. These substances can occur in combination or solely in a number of plants by nature. Further additions to such toothpastes and mouthrinses are extracts of chestnut, sometimes in combination with urea (EP-A-108.318). Sometimes such toothpastes and mouthwashes also contain chlorhexidine (EP-A-038.876). Also is sometimes added to such toothpastes and mouthrinses an extract of St. John's Worth, either or not in combination with pyruvic acid, L-Borneol, and/or Bornylacetate (EP-A-117.905). SU appl. No. 712.087 describes utilization of the combination of carbonic acid extracts of grape seeds, juniper berries and peppermint for good regeneration-trophic properties. SU appl. No. 615.932 describes the combination of carbonic acid extract of juniper berries with an aqueous-alcoholic infusion of eucalyptus for improvement of treatment-prophylaxis. Application of various japanese plantextracts in mouthwaters, such as: *Prynaria fortunei*, and oriental arborvitae, a burnet, a lotus root, a mugwort, a hiba arborvitae, leaves of a japanese cedar, a podocarp, a japanese nutmet, and juniper berry leaves suggest strong inhibiting action of plasmin and urokinase activity and having improved fleeding arresting effect according to Jap. appl. No. 55-120.509. SU appl. No. 558.675 describes utilization of the combination of aqueous-alcoholic extracts of nettle, st. John's Worth, sage and elder in a toothpaste to obtain an effective cleaning and deoderising effect. SU appl. No. 434.944 describes the application in a toothpaste of an aqueous-alcoholic extract of nettle together with polyvinyl pyrrolidon in which the nettle extract is claimed to have preventive medicinal activity.

The application of these active ingredients resides mainly in the anti-bacterial effects these active ingredients have on plaque accumulation. This oral plaque is a substance containing live as well as dead micro-organisms, the remains of food and metabolic products of those micro-organisms (toxins). The effect of the active ingredients is either directed against the micro-organisms themselves, or at the extra-cellular matrix in plaque. The consequence of this is mostly so that plaque accumulation is reduced and the formation of new plaque is inhibited. This effect is naturally also reached through good mechanical cleansing (e.g. toothbrushing, toothpicks and flossing). However, the interdental spaces, in general, are insufficiently reached with this mechanical cleansing only. Active ingredients in both mouthrinses and toothpastes can, however, reach those areas which are difficult to reach mechanically. The effect of toothpastes with these active ingredients resides therefore in a combined mechanical/biological/-chemical principle, those of mouth-rinses in a chemical/biological principle. The active ingredients may, however, not have any harmful side-effects, which is not always the case. For chlor-hexidine, if used continuously, it is known e.g., that this ingredient will contribute to heavily staining both teeth and molars, whilst composite fillings, if present, will turn even darker.

Dental researchers have demonstrated, that, perhaps with the exception of localized juvenil periodontitis, that the origins of gingivitis and consequently periodontitis go together with the presence of plaque and/or calculus. The metabolites derived from plaque are apparently able to initiate these disease processes as are the micro-organisms themselves. A solution, where constantly, and without interruption, plaque disappears and remains absent, shall create a world without gingivitis and periodontitis. It is therefore of utmost importance to keep plaque accumulation under control. Considering the human nature, which is not structured to faultless systematic use of tools for the cleansing of plaque, it is considered desirable to make such a substance available, that by irregular use of this substance, the best result will be approached. An ideal mouthcare-product, be it a toothpaste or a mouthrinse, should therefore contain, next to possible cleansing-agents in line with the mechanical principle, one or more substances, which:

a) eliminate as far as possible harmful micro-flora,
b) neutralise as far as possible metabolites of the micro-organisms present,
c) raise the resistance of the human body by means of aid to specialist defence-cells against those harmful micro-organisms and their products,
d) are not harmful themselves in therapeutic dosis to humans.

This invention relates to addition of substances to mouthcare products, aimed at reaching the object described hereabove and are successful in doing so. This invention is based on an unknown and surprising synergetic effect by using two of these plant extracts together in mouthcare-products.

The invention provides mouthcare-products, such as toothpastes, mouthrinses, and medicinal mouthcare compositions characterized by the fact that they contain (a) an extract of *Urtica dioica* (nettle), and (b) an extract of *Juniperus communis* (juniper). Each of these extracts may be replaced by one or more of the medicinal-active components residing in those extracts. A further slight increase in effectivity is obtained by the addition of c) *Achillaea millefollum* to extracts of a) and b). Preferably extracts based on a water/propylene-glycol-basis are used, but also other aqueous solutions, alcoholic solutions and aqueous/alcoholic (e.g. isopropanol) solutions and solutions of the extracts in oil are applicable. In principle all possible extract-form is applicable.

As an extract of a) one should prefer the use of an extract of the leaves (*Urtica dioica e folia*), and as an extract of b) one should prefer the use of the extract of the fruits (*Juniperus communis e fructus*) and as an extract of c) one should prefer the use of the extracts of the leaves and blossom. (*Achillaea millfollum e herb e flor*). More detailed information can be obtained from: M. Wichtel: Teedrogen, Wissenschaftliche Verlagsgesellschaft mbH, Stuttgart, 1984, pp. 85, and in: Hager's Handbuch der pnarmaceutische Praxis 4. Neuausgabe Springer Verlag, Bd. 6, pp. 360, as well as in H. A. Hoppe Drogenkunde, Bd. 1, pp. 1104, relating to extracts of a).

In H. A. Hoppe's Drogenkunde Bd. 2, pp. 200, and in: W. de Gruyter, 1975, and in M. Wichtl., Teedrogen, pp. 346 relating to extracts of b).

In: H. A. Hoppe's Drogenkunde Bd. 1 pp. 11 and in Merck Index 9th. edition pp. 11 and in Martindale, the extra-Pharmacopoeia, 27th edition, pp. 1011 relating to extracts of c).

The use of tinctura's is also possible. The extraction-process itself has been described in many pharmacopaeas. See: Martindale: The Extra Pharmacopoeia 27th edition, pharmaceutical Press, London, 1978. The preferred concentrations of extracts a), b) and c) in the mentioned mouthcare and toothcare-products is for extracts of a): between 0.1 and 3.0% by weight, and for
b): between 0.1 and 2.0% by weight, and for
c): between 0.1 and 2.0% by weight.

For the combination of extracts a) plus b) the preferred concentrations should be between 0.1 and 3.0% by weight, while for the combination of a) plus b) plus c) the preferred concentration is also between 0.1 and 3.0% by weight.

These mentioned percentages of extract, added to the mouthcare-products, are being calculated on the basis of a mixture water:propylene-glycol extract, in which mixture propylene-glycol takes about 40% by weight and the rest is taken up by water. Herewith is 1 kg of such an extract corresponding to 1 kg of the original plant parts.

In lieu of the extracts, also the active substances contained in them, and responsable for the medicinal effect, can be applied. These substances can be isolated from the extracts or been obtained by organic synthesis.

The effects of the according to this invention applied extracts or the medicinal-active substances contained in them, is healthcaring action on the gingiva as well as on the underlying tissues in the mouth, reduce dental plaque and above all reduction or inhibition of bleeding or inflammation of the gingiva (gingivitis). This effect is present with the extracts separately. When however extracts a) and b) are used in combination with each other, surprisingly a strong synergistic effect is being remarked, through which the total percentage of the extracts-combination, applied in mouth-care products, can be lowered compared with the percentages of the separate extracts in application to these products and obtaining an even more pronounced response. An even slightly better result is being obtained by applying extract c) in addition to extracts a) plus b). The results of this original experimental testing in clinic are summarized in table 1.

TABLE 1

Summary of original experimental clinical test results. Results are measured after 4 weeks application.

| | | reduction of plaque index percentage of baseline | reduction of bleeding index percentage of baseline |
|---|---|---|---|
| 1. | c) at 1.8% | 8.3 | 13.2 |
| 2. | b) at 1.8% | 13.6 | 18.8 |
| 3. | a) at 1.8% | 11.3 | 16.2 |
| 4. | a) + b) together 1.8% | 32 | 46 |
| 5. | b) + c) together 1.8% | 15.3 | 14.7 |
| 6. | a) + c) together 1.8% | 19.0 | 17.6 |
| 7. | a) + b) + c) together 1.8% | 33 | 52 |
| | placebo | 4.4 | 6.2 |

Noticeable is that the combination of a) plus b) at a total concentration of exactly the same level as the two extracts were used separately (concentration a)+b)-=concentration a)=concentration b)) raised the response to ca. 2.5-fold. The result is slightly higher by adding extract c) to the combination of extracts a)+b).

The mechanism which is underlying these effects is to a certain extent unknown. However, certain aspects of its mechanism have now been cleared through testing. The plant extracts yield a selective anti-bacterial effect in minimum inhibitory concentration and zone of inhibition tests in vitro. Bacterial species, which are generally held responsable for periodontal diseases, and most often are found in sites of disease, are being inhibited exclusively. Other micro-organisms in the mouth are not effected by these combinations of plant extracts.

A summary of these in vitro test-results is seen in table 2.

TABLE 2

Test-results of zones of inhibition on different strains of bacterial species with compound a) + b) + c).

| bacterial strains | Zones of inhibition (radius in mm) compound |
|---|---|
| gram-positive cocci: | a) + b) + c) |
| Str. mutans R9 | 0 |
| Str. sobrinus ATCC 2-27351 B 13 | 0 |
| Str. sanguis NCTC 7865 | 0 |
| Str. mitior EF 186 | 0 |
| Str. milleri CTC 10709 | 0 |
| rods: | |
| *Actinomyces viscosus* WVU 627 | 0 |
| *Actinomyces naeslundi* | 55 |
| *Lactobacillus casei* AC 413 | 0 |
| *Rothia dentocariosa* | 1 |
| gram-negative cocci: | |
| *Neisseria subflava A 1078* | 8 |
| *Veillonella alkalescens* ATCC 17745 | 1.5 |
| rods: | |
| *A. actinomycetemcomitans* NCTC 9710 | 7 |

TABLE 2-continued

Test-results of zones of inhibition on different strains of bacterial species with compound a) + b) + c).

| bacterial strains | Zones of inhibition (radius in mm) compound |
|---|---|
| idem NCTC 10979 | 5 |
| idem Y 4 | 5 |
| Capnocytophage 16 209 | 6 |
| C. sputagena BM 1975 | 7 |
| Haemopphilus aphrophilus 5906 | 2 |
| H. paraphrophilus | 1 |
| Bacteroides melaninogenicus 4196 | 1 |
| Bacteroides intermedius T 588 | 3 |
| Bacreroides gingivalis W50 | 10 |
| Fusobacterium nucleatum NCTC 10953 | 3 |

Another additional activity was noted during the testing of antibacterial activity. Application of the plant extract combination to S.mutans reduced the glycolysis. This gives rise to the expectation that also cariogenic effects derived from S.mutans are reduced.

Another interesting effect being measured in this in-vitro studies is the inhibition of a trypsin-like protease from B.gingivalis. This bacterial protease is very suspect for unspecific protealysis of supporting tissues of the dentition. For further understanding of the working mechanism, biochemical work with clinical testing is in progress.

In clinical research-programs, executed after the original experimental work, it has been established, that test-persons, applicating a mouthcare-product according to this invention, showed significant reduction of inflammation-parameters, compared to placebo in a double blind cross-over test. The purpose of these clinical tests was to establish the effects on plaque accumulation and gingivitis of a toothpaste containing the mixture of plant extracts. These tests were performed in 56 patients with plaque accumulation ($\bar{x}PI=2.15$) and gingivitis ($\bar{x}PBI=2.20$) and ($\bar{x}SFFR=1.90$) during a five month period.

PI = plaque index,
PBI = papillary bleeding index,
SFFR = sulcus fluid flow-rate.

Experimental Procedure

The effect of the test-toothpaste with active plant extracts was evaluated and compared with a placebo toothpaste, unknown dentifrices and baseline measurements in a double blind crossover study. Measurements were taken on mesial surfaces of elements 11-17 plus 41-47 or by choice on mesial surfaces of elements 21-27 plus 31-37. The brushing techniques and other oral hygiene measurements of the participants of group 1 and 2 were deliberately left unchanged. New toothbrushes of one brand were used. All participants received the brushes and toothpaste after baseline measurements.

Evaluation of the recorded scores in the test period, with recalls every 10 days, were as follows: from day 0 until day 30 group 1 used the test toothpaste, while group 2 used the placebo. From day 30 to day 60 all participants from both groups were using their own brand of toothpaste again. From day 60 to day 90 group 2 used the test dentifrice, while group 1 used the placebo. Results of the clinical testprogram are summarized in table 3.

TABLE 3

Mean PI-, PBI-, and SFFR scores (sd left out) after using a test- and placebo toothpaste in a double blind cross-over testprogram for 90 days

| day | 0 | | 30 | | 60 | | 90 | |
|---|---|---|---|---|---|---|---|---|
| group | 1 | 1 | 1 | 2 | 1 | 2 | 1 | 2 |
| toothpaste | own | own | test | plac. | own | own | plac. | test |
| subject no. | 24 | 21 | 24 | 21 | 24 | 21 | 24 | 21 |
| PB | 2,2 | 2,1 | 1.7 | 1.8 | 2.0 | 1.9 | 1.9 | 1.7 |
| PBI | 2.1 | 2.3 | 1.2* | 1.9 | 1.9 | 2.0 | 1.8 | 1.0* |
| SFFR | 1 8 | 2.0 | 0.9* | 1.9 | 1.9 | 1.9 | 1.9 | 0.9* |

*Stat. sign. pF 0.01

This invention, aimed at the conservation of healthy supporting tissues around the dention of human beings, in therefore based on the use of the combination of these active plant extracts, which have never before been used together for this purpose and are: a) plaque-reducing because of a bacteriocidal effect, and b) anti-inflammatory in a measure which cannot only been explained from the anti-plaque effect. The combination of plant extracts are effective, active ingredients, can be applied into toothpastes, mouthwaters, and medicinal mouthcare preparations by using well-known techniques.

Safety tests on the combined mixture of the plant extracts have resulted in the following data:
1. Acute Oral Limit Test in rats: no clinical signs and no death at a dose level of 1800 mg/kg.
2. Acute Dermal Irritation Test in rabbits: Negative.
3. Acute Eye Irritation Test in rabbits: Negative.

Besides the application of the plant extract mixture in toothpastes and mouthwashes, is another realistic application the used by dentists and dentists-specialists as a locally applied irrigation medium in the mouth. The use of a sub-gingivally applied irrigation liquid containing the active plant extracts, by means of a hollow syringe, directed into gingival pockets and from there irrigated is in this aspect typical. The effluent is to be aspired and discarded by an assistent. This treatment can be performed in cases of serious gingivitis and periodontitis as well as preventive to periodontal surgery. Also postoperatively it can be very helpful to continue these irrigations during reconstitution.

The plant extract combination of the present invention can be used in toothpastes of different kinds, gels, pastes and creams, which can be translucent, opaque or transparent. As examples of abrasives in toothpastes containing the plant extract combination can be mentioned: phosphates, such as dicalcium phosphate, calcium pyrophosphate and insoluble sodium metaphosphate, silicas (precipitated or xerogel), calcium carbonate (precipitated or natural) and hydrated aluminium oxide. Humectants are conventional components of toothpastes and as examples of such can be mentioned glycerol, sorbitol, xylitol, poly-ethylene glycol and polypropylene glycol.

Another group of toothpaste components are the gelling agents, which can also act as binders or stabilizers and as examples of suitable such compounds can be mentioned cellulose ethers, such as sodium carboxy methyl- or hydroxyethyl cellulose, xanthan gums and gums of natural origin such as carrageenan and alginates, non-abrasive silicas and synthetic polymers such as carboxyvinyl polymers.

Surface-active agents are conventionally used and are normally anionic, nonionic or amphoteric. As examples of suitable anionic agents can be mentioned higher alkyl sulphates such as sodium laurylsulphate, alkylaryl sulphonates, sulfonated monoglycerides from fatty acids and sarcosinates. Suitable nonionic surfactants are for example ethylene oxide condensates of alkyl phenols and fatty alcohols.

In fluoro-containing toothpastes the fluoride source can be for example sodium fluoride, stannous fluoride, sodium monofluorophosphates and amine fluorides. Other additives that may be used in the toothpastes include pH-buffering and -stabilising components such as combinations of monosodium and trisodiumphosphate antibacterial and anti-plaque agents such as quaternary ammonium compounds, chlohexidine and other b guanide compounds, zinc citrate and trichlorodiphenyl ether, anticalculus agents such as pyrophosphates, phosphonic acid derivatives, polyaminopolyphosphonates and benzoates. Flavouring and sweetening agents, for example sodium saccharinate, preservatives, such as methyl-, propyl- and butylesters of para-hydroxybenzoic acid and salts of benzoic acid, colouring agents and whitening agents such as titanium dioxide are most often also included in the toothpastes. All of the above mentioned components can be used in toothpastes containing the plant extract combination of this invention and can be included in the conventional amounts.

The water content of toothpastes is generally between 5 and 45% while for mouthwashes the water content generally is between 45 and 90%. Mouthwashes in addition usually contain alcohol, preferably ethanol or isopropyl alcohol, surface active agents and antibacterial agents.

EXAMPLES

The following toothpastes with the combination of the plant extracts a) and b) and sometimes c) have been prepared:

Example 1: Composition of an Active Toothpaste Based on Dicalcium Phosphate

| Example 1: | |
|---|---|
| Glycerol 86% | 20 g |
| Sorbitol 70% | 10 g |
| Na-carboxymethyl cellulose | 2 g |
| Demi water | 27.5 g |
| Dicalc. phosphate | 35 g |
| Na-dodecyl sulphate | 2 g |
| Na-saccharine | .2 g |
| Na monofluorophosph. | .2 g |
| Benzoe acid m-ester | .1 g |
| Benzoe acid p-ester | .1 g |
| Flavour | 1.1 g |
| Plant extr. combin. | 1.8 g |
| | 100 g |

During processing of the toothpaste, the plant extracts are preferably applied to the mix after all other ingredients have been added, but before the flavour is added.

The following toothpastes with silica abrasive including the plant extract combination of a) plus b) and also sometimes c) have also been prepared. Formulation I is a translucent toothpaste, formulation II is a transparent and formulation III is an opaque toothpaste

| Components | Amount, % by weight formulation | | |
|---|---|---|---|
| | I | II | III |
| Silicas, abrasive | 8 | 8 | 9 |
| Silicas, thickening | 10 | 10 | 11 |
| Sorbitol (70%) | 55 | 68 | 35 |
| Sodium-fluoride | .2 | .2 | — |
| Sodium lauryl sulphate | 1 | 1 | 1 |
| Carboxymethyl cellulose | .6 | .4 | 1.0 |
| Polyethylene glycol | 4 | 4 | 4.5 |
| Plant extract combination | 1.7 | 1.7 | 1.7 |
| Preservatives, colours, flavours | q.s | q.s | q.s |
| Water to 100% | | | |

Further toothpastes with combinations of abrasive including the plant extract combinations are the following:

| Components | Amount, % by weight formulation | |
|---|---|---|
| | IV | V |
| Alumina | 10 | 25 |
| Calcium carbonate | — | 10 |
| Silicas, abrasive and/or thickening | 18 | — |
| Sorbitol (70%) | 33 | 30 |
| Cellulose gum | 1.1 | 1.2 |
| Sodium lauryl sulphate | .9 | — |
| Sodium monofluorophosphate | .8 | .8 |
| Plant extract combination | 2.5 | 2.5 |
| Preservatives, colours, flavours | q.s | q.s |
| Water to 100% | | |

Another prepared toothpaste is the following:

| Component | Amount, % by weight formula VI |
|---|---|
| Alumina | 45 |
| Silica, thickening | 3 |
| Sorbitol (70%) | 27 |
| Cellulose gum | 1.2 |
| Sodium monofluorophosphate | .8 |
| Plant extract combination | 1.5 |
| Preservatives, colours, flavours | q.s |
| Water to 100%. | |

Toothpastes produced according to these formulations yield in use after a very short time a pleasant smooth surface and clean feeling besides a remarkable reduction in plaque-accumulation and a significant reduction of the gingival bleeding-index.

Example for a mouthwater:

| Component | Amount, % by weight |
|---|---|
| Ethyl-alcohol | 4 |
| Flavour | 2 |
| Plant extracts combination | 2.5 |
| Demi water to 100% | |

A mouthwash, produced according to this formulation, yields in use after a very short time a noticeable reduction of plaque-accumulation and an important lowering of the gingival bleeding-index together with a general fresh taste.

Example for an irrigation-liquid

| Component | Amount, % by weight |
| --- | --- |
| Ethyl-alcohol | 5 |
| Active plant extracts combination | 3 |
| Anionic surfactant | 1 |
| Freshly boiled demi-water to 100% | |

I claim:

1. A mouthcare composition consisting essentially of:
   (a) an extract of leaves of *Urtica dioica* in a concentration of 0.1–3.0% by weight; and
   (b) an extract of fruits of *Juniperus communis* in a concentration of 0.1–2.0% by weight,
   wherein (a) and (b) together total 1.8% by weight.

2. A mouthcare composition consisting essentially of:
   (a) an extract of leaves of *Urtica dioica* in a concentration of 0.1–3.0% by weight;
   (b) an extract of fruits of *Juniperus communis* in a concentration of 0.1–2.0% by weight; and
   (c) an extract of leaves or blossoms of *Achillaea millefolium* in a concentration of 0.1–2.0% by weight, wherein (a), (b) and (c) together total 1.8%.

3. A method of mouthcare which comprises applying to the mouth a composition consisting of:
   (a) an extract of leaves of *Urtica dioica* in a concentration of 0.1–3.0% by weight; and
   (b) an extract of fruits of *Juniperus communis* in a concentration of 0.1–2% by weight, wherein (a) and (b) together total 1.8% by weight.

4. A method of mouthcare which comprises applying to the mouth a composition consisting of:
   (a) an extract of leaves of *Urtica dioica* in a concentration of 0.1–3.0% by weight;
   (b) an extract of fruits of *Juniperus communis* in a concentration of 0.1–2.0% by weight; and
   (c) an extract of leaves or blossoms of *Achillaea millefolium* in a concentration of 0.1–2.0% by weight, wherein (a), (b) and (c) together total 1.8% by weight.

* * * * *